(12) United States Patent
Hohmann et al.

(10) Patent No.: US 7,001,576 B2
(45) Date of Patent: Feb. 21, 2006

(54) EMULSIFYING AND SEPARATING DEVICE FOR LIQUID PHASES

(75) Inventors: Michael Hohmann, Darmstadt (DE); Michael Schmelz, Kriftel (DE); Günter Brenner, Griesheim (DE); Hanns Wurziger, Darmstadt (DE); Norbert Schwesinger, Ilmenau (DE)

(73) Assignee: Merck Patent GmbH, Darmstadt (DE)

( * ) Notice: Subject to any disclaimer, the term of this patent is extended or adjusted under 35 U.S.C. 154(b) by 2 days.

(21) Appl. No.: 10/296,063

(22) PCT Filed: May 9, 2001

(86) PCT No.: PCT/EP01/05283

§ 371 (c)(1),
(2), (4) Date: Sep. 11, 2003

(87) PCT Pub. No.: WO01/89693

PCT Pub. Date: Nov. 29, 2001

(65) Prior Publication Data

US 2004/0026305 A1    Feb. 12, 2004

(30) Foreign Application Priority Data

May 23, 2000    (DE) .............................. 100 25 699

(51) Int. Cl.
*B01L 3/00*    (2006.01)
*B01F 5/06*    (2006.01)

(52) U.S. Cl. ..................... 422/224; 422/129; 422/187; 366/338; 366/339; 210/511

(58) Field of Classification Search ................ 422/129, 422/187, 224; 366/339, 338; 210/511
See application file for complete search history.

(56) References Cited

U.S. PATENT DOCUMENTS

| 5,595,712 | A | 1/1997 | Harbster et al. |
| 5,803,600 | A | 9/1998 | Schubert et al. |
| 6,306,590 | B1 * | 10/2001 | Mehta et al. ................. 435/6 |

FOREIGN PATENT DOCUMENTS

| EP | 0 988 886 | 3/2000 |
| WO | WO 98 10267 | 3/1998 |
| WO | WO 99 64848 | 12/1999 |

* cited by examiner

*Primary Examiner*—David A. Reifsnyder
(74) *Attorney, Agent, or Firm*—Millen, White, Zelano & Branigan, P.C.

(57) ABSTRACT

A device for the emulsification and separation of small amounts of immiscible liquid phases has essentially a cover plate (2), which can be tightly connected to a base plate (1), where microchannels (4,4a,5,6,6a) in the form of grooves are cut out on the inner surface (3,3a) of the base plate (1) and/or cover plate (2). In a mixing zone, two microchannels (4,4a) run in a wave shape crossing one another a number of times. In a subsequent separation zone, they run essentially straight combined in a common microchannel (5). The otherwise tightly sealed-off microchannels (4,4a,5,6,6a) can be filled and emptied again via inlet apertures (8,8a) and outlet apertures (9,9a).

10 Claims, 2 Drawing Sheets

EMULSIFYING AND SEPARATING DEVICE FOR LIQUID PHASES

The invention relates to a device for the emulsification and separation of small amounts of immiscible liquid phases.

The use of new technologies enables a drastic reduction in the characteristic dimensions when carrying out chemical reactions. Chemical processes which it has hitherto only been possible to implement in large plants can be carried out on a laboratory scale using miniaturised microcomponents. Owing to constant further development of manufacturing techniques for microreaction systems, a wide range of processes and materials are now available for the production of microreaction systems. The use of extremely temperature- and acid-resistant materials for the production of microreaction systems has only recently facilitated controlled reactions with highly concentrated acids or the performance of gas-phase processes at high temperatures. Owing to the small amounts of chemical substances participating in the reaction, highly exothermic or endothermic reactions can also be carried out at controlled, in particular constant temperature. Besides, inter alia, economic advantages, miniaturisation thus leads to completely new research opportunities in many areas of industrial chemistry and process engineering and a constant broadening of the range of applications.

The path to a miniaturised, continuous plant on a laboratory scale has hitherto primarily involved the development of individual microcomponents, such as pumps, mixers, reactors and heat exchangers; connection thereof in series enables chemical reactions to be carried out continuously in through-flow. However, the larger the spatial distance between separately manufactured microcomponents of this type, the more complex and difficult is precise control of the reaction parameters during the reaction, for example of the individual concentrations of substances participating in the reaction and the temperature or input of energy. During emulsification and subsequent separation, identical reaction conditions, such as, for example, the temperature, can only be guaranteed at very great effort, if at all.

The object of the invention is therefore to provide an emulsification and separation device for two immiscible liquid phases in which the identical reaction conditions can be specified for the two process steps.

This object is achieved in accordance with the invention on the basis of a device which has a base plate and a cover plate which can be connected thereto, with microchannels cut out in the form of grooves on the inner surface of the base plate and/or cover plate, where two microchannels which can be filled separately through fill apertures in the base plate and/or cover plate cross one another a number of times in a mixing zone, the microchannels run together in a common microchannel in a subsequent separation zone, and, after a subsequent branch, are run to separate outlet apertures.

There is consequently no spatial separation between the emulsification of two immiscible liquid phases and the subsequent separation. It is therefore possible using means of simple design to ensure identical ambient conditions for the two process steps.

The emulsion formation, which is highly dependent on the geometry, may be affected by the shaping of the microchannels, in particular the size of the mixing or separation zone. The cross-sectional shape and surface structure of the cut-out microchannels can easily be matched to any desired application by means of precision-mechanical manufacturing methods. The base plate and cover plate can optionally be made of metals, plastic or glass, each of which is suitable for certain chemical reactions, enabling use with an extremely wide variety of chemical substances.

Since machining is only necessary in the immediate surface region of the base plate or cover plate, the manufacturing complexity necessary for the production of the entire device is relatively low. Owing to the simple design, the device can be operated with virtually no maintenance, even in the long term. If a tight connection of the base plate to the cover plate is not effected through a material connection, but instead merely through pressure, the base plate and cover plate can easily be taken apart and cleaned in a simple manner.

According to an embodiment of the inventive idea, either only the base plate or only the cover plate has microchannels cut out in the form of grooves. Instead, however, it is also possible to cut microchannels out on the corresponding surface of both the base plate and the cover plate.

According to an advantageous embodiment of the inventive idea, it is provided that the base plate and/or the cover plate has devices for temperature control. An important property of microreaction systems is the large surface area of the microchannels relative to the liquid volume. Effective control and regulation of the heat balance is therefore possible, even in the case of highly endothermic or exothermic reactions. This is achieved in a simple manner by temperature control of the base plate and/or cover plate. Owing to the small cross sections of the microchannels and the resultant low volume flow rates, good heat exchange is ensured.

It is preferably provided that the base plate and the cover plate can be connected tightly by screws. A connection which is usually sufficiently tight, even over long periods, is produced by screwing. However, the base plate and cover plate can be separated from one another again, for example for simplified cleaning.

According to an embodiment of the inventive idea, it is provided that the outlet apertures of a device for the emulsification and separation of immiscible liquid phases can be connected to the inlet apertures of an adjacently arranged device. This facilitates multistep extraction by connecting a plurality of devices in series. Reaction mixtures can thus be worked up continuously, even on a small scale.

Further advantageous embodiments of the inventive idea are the subject-matter of embodiments described herein.

An illustrative example of the invention which is shown in the drawing is explained in greater detail below.

The single figure shows an exploded three-dimensional view of a device consisting of a base plate and a cover plate.

The illustrative example shown of the emulsification and separation device consists of a flat, rectangular base plate 1 and a cover plate 2 of similar shape. Microchannels 4,4a, 5,6,6a cut out in the form of grooves are located on a surface 3 of the base plate 1 facing the cover plate 2. Two microchannels 4,4a run on one side of the surface 3 in a wave shape crossing one another a number of times. This zone, referred to below for simplification as the mixing zone, terminates approximately in the centre of the surface 3 of the base plate 1, where the two microchannels 4,4a combine to form a common microchannel 5. The common microchannel 5 runs essentially straight. In this zone, referred to below for simplification as the separation zone, separation of the immiscible liquid phases takes place on the basis of different physical properties, such as, for example, the surface tension.

Just before the end of the surface 3 of the base plate 1, the common microchannel 5 splits again into two outlet channels 6,6a. For tight connection of the base plate 1 and the cover plate 2 one above the other, six screw holes 7, which are symmetrically distributed at the edges of the base plate 1 and of the cover plate 2, are provided in each. Two inlet apertures 8,8a and two outlet apertures 9,9a designed as cylindrical holes are located in the cover plate 2, which covers the surface 3 of the base plate 1. If the base plate 1 and the cover plate 2 are connected tightly, the two microchannels 4,4a can be filled with liquid phases through the respectively assigned inlet apertures 8,8a. The liquid phases flow through the mixing zone, where effective emulsification of the two phases takes place. After separation of the two phases in the subsequent separation zone, the two phases exit again separately through the respective outlet apertures 9,9a.

It is also possible for microchannels likewise designed in the same way as grooves to be cut out on the inner surface 3a of the cover plate 2. The base plate 1 and the cover plate 2 may also be arranged differently, in particular the arrangement of the base plate 1 and of the cover plate 2 may be interchanged.

Another conceivable design variant is one in which one or more intermediate plates between the base plate 1 and the cover plate 2 can be tightly connected thereto and each have microchannels cut out on the inner surfaces.

Figure 1:
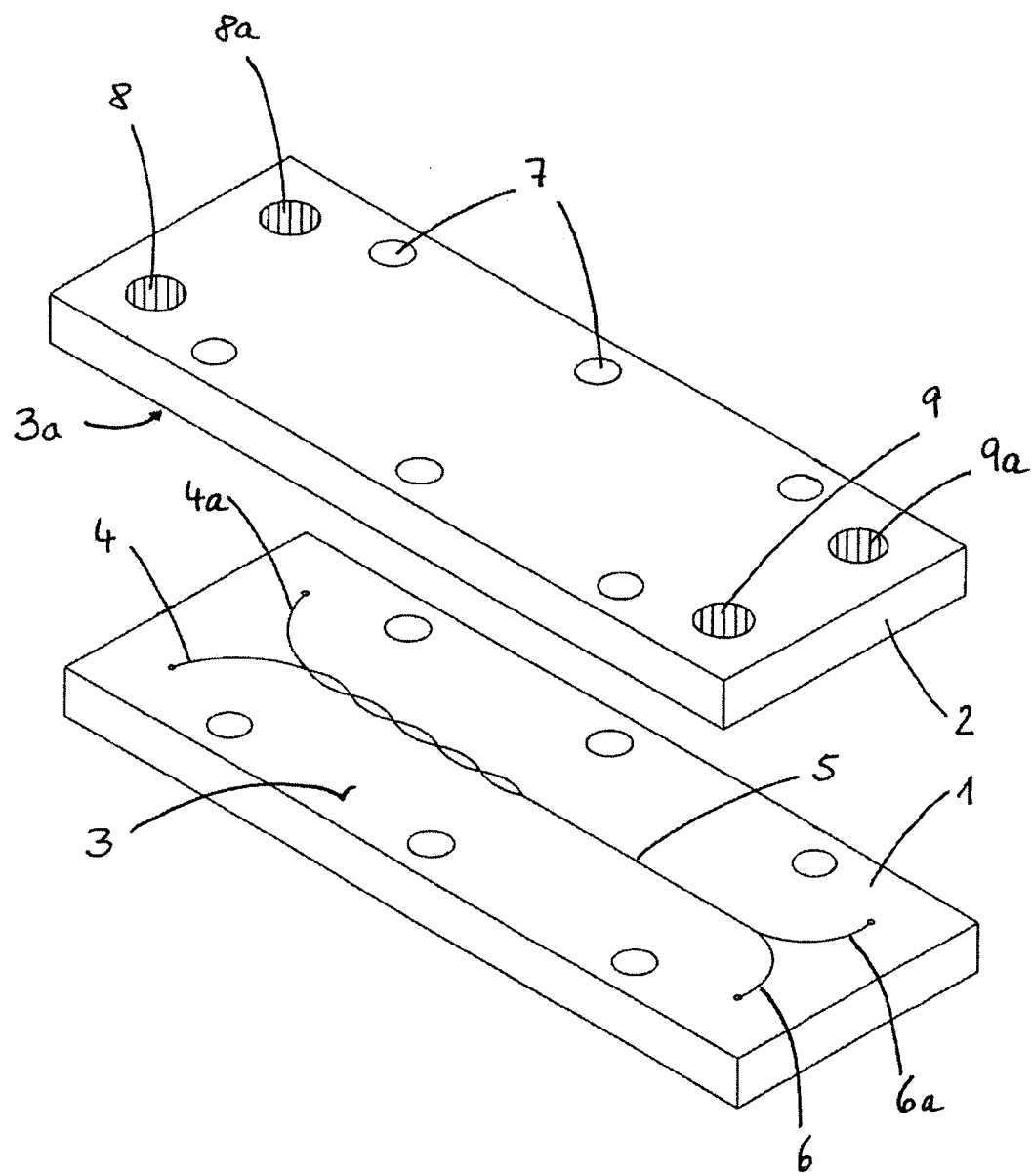
FIG. 1: Illustrates an embodiment of the invention having a base plate (1) and cover plate (2).
Figure 2:
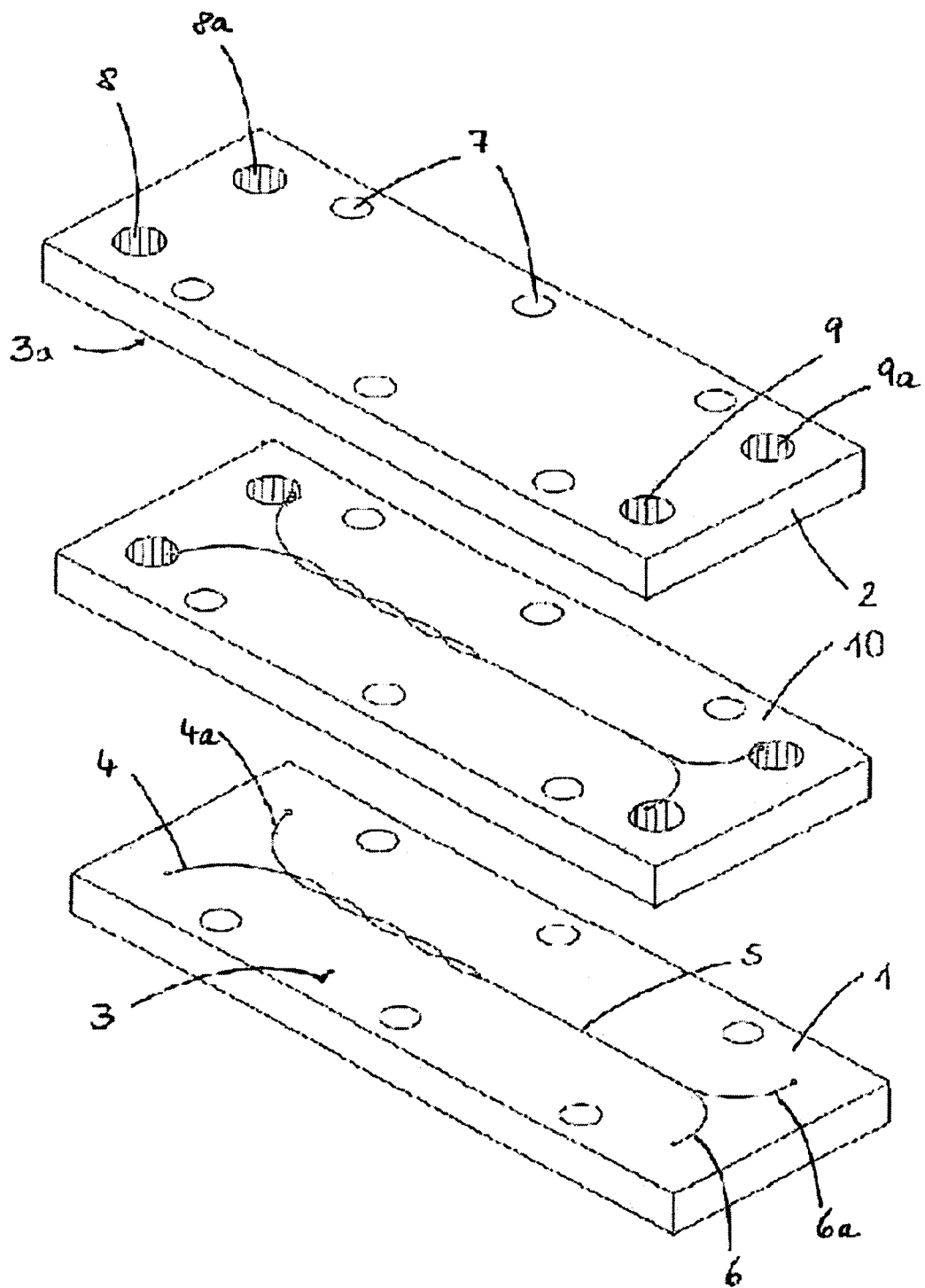
FIG. 2: illustrates an embodiment of the invention where an intermediate plate (10) is present between the base plate (1) and cover plate (2).

What is claimed is:

1. A device for the emulsification and separation of small amounts of immiscible liquid phases comprising a base plate having an inner surface and a cover plate having an inner surface, which plates can be connected together, with said inner surfaces facing inward, with microchannels cut in grooves on the inner surface of the base plate and/or cover plate, wherein two microchannels, which can be filled separately through fill apertures in the base plate and/or cover plate, cross one another a number of times, forming a mixing zone sufficient to form an emulsion, and wherein at a subsequent point the two microchannels run together in a common microchannel, which is a separation zone sufficient to spatially separate said immiscible liquid phases within said common microchannel, and wherein at a subsequent point said common microchannel is divided into two microchannels, one of which divided microchannels is spatially located at a first spatial location to receive essentially only one of said immiscible liquid phases and the other of which divided microchannels is spatially located at a second spatial location which is different than the first spatial location to receive essentially only the other one of said immiscible liquid phases, and which divided microchannels run to separate outlet apertures.

2. A device according to claim 1, wherein the two microchannels crossing one another in the mixing zone run in a wave shape.

3. A device according to claim 1, wherein the common microchannel runs essentially straight.

4. A device according to claim 1, wherein either only the base plate or only the cover plate has microchannels.

5. A device according to claim 1, wherein the base plate and/or the cover plate has a device for temperature control.

6. A device according to claim 1, wherein the base plate and the cover plate are tightly connected together by screws.

7. A device according to claim 1, whose outlet apertures are connected to fill apertures of an adjacently arranged device.

8. A device according to claim 1, having one or more intermediate plates between the base plate and the cover plate, each of said one or more intermediate plates has two inner surfaces with microchannels on one or both of the two inner surfaces, with one of the two inner surfaces facing the base plate and the other of the two inner surfaces facing the cover plate.

9. A device according to claim 8, wherein the microchannels on the one or more intermediate plates is arranged the same as the microchannels on the base and/or cover plate.

10. A device according to claim 1, which does not contain an intermediate plate.

* * * * *